United States Patent

Hoelzl et al.

(10) Patent No.: US 8,274,280 B2
(45) Date of Patent: Sep. 25, 2012

(54) DEVICE AND PROCESS FOR NONDESTRUCTIVE AND NONCONTACT DETECTION OF FAULTS IN A TEST PIECE

(75) Inventors: Roland Hoelzl, Munich (DE); Bernd Zimmermann, Ihringen (DE)

(73) Assignee: Pruftechnik Dieter Busch AG, Ismaning (DE)

( * ) Notice: Subject to any disclaimer, the term of this patent is extended or adjusted under 35 U.S.C. 154(b) by 556 days.

(21) Appl. No.: 12/543,001

(22) Filed: Aug. 18, 2009

(65) Prior Publication Data

US 2010/0039102 A1 Feb. 18, 2010

(30) Foreign Application Priority Data

Aug. 18, 2008 (DE) .................. 10 2008 038 174

(51) Int. Cl.
*G01N 27/82* (2006.01)
(52) U.S. Cl. ........................ 324/240; 324/239
(58) Field of Classification Search .................. 324/239, 324/240
See application file for complete search history.

(56) References Cited

U.S. PATENT DOCUMENTS

| | | | |
|---|---|---|---|
| 4,445,088 A | 4/1984 | Schübel | |
| 5,175,498 A | 12/1992 | Cueman et al. | |
| 6,344,740 B1 | 2/2002 | Häberlein | |
| 2001/0040683 A1 * | 11/2001 | Hofman | 356/635 |

FOREIGN PATENT DOCUMENTS

| | | |
|---|---|---|
| DE | 40 03 330 A1 | 8/1991 |
| DE | 44 21 912 A1 | 1/1996 |
| DE | 101 14 961 A1 | 10/2002 |
| DE | 10 2006 048 954 A1 | 4/2008 |
| EP | 0 440 931 A1 | 8/1991 |
| EP | 1 154 226 A2 | 11/2001 |
| EP | 1 747 848 A1 | 1/2007 |
| GB | 2 014 317 A | 8/1979 |
| WO | 03/102496 A1 | 12/2003 |

* cited by examiner

*Primary Examiner* — Reena Aurora
(74) *Attorney, Agent, or Firm* — Roberts Mlotkowski Safran & Cole, P.C.; David S. Safran

(57) ABSTRACT

A device for nondestructive and noncontact detection of faults in a test piece, with a stationary measurement device (16) for taking an eddy current or a magnetic stray flux measurements on a test piece (10) continuously advanced relative to the measurement device; and a device (12) for positioning the test piece with respect to the measurement device in a plane perpendicular to the direction of movement of the test piece. The device also has a monitoring unit (20) with at least three distance sensors (22) arranged distributed around the test piece in the peripheral direction for contactless detection of the distance between the surface of the test piece facing the respective sensor and the respective sensor, as well as a unit for evaluating the signals from the sensors.

15 Claims, 1 Drawing Sheet

DEVICE AND PROCESS FOR NONDESTRUCTIVE AND NONCONTACT DETECTION OF FAULTS IN A TEST PIECE

BACKGROUND OF THE INVENTION

1. Field of Invention

This invention relates to a device for nondestructive and noncontact detection of faults in a test piece by means of eddy current measurement or magnetic stray flux measurement having a stationary measurement means for taking an eddy current measurement or a magnetic stray flux measurement on a test piece which is continuously advanced relative to a measurement means; and a means for positioning the test piece with respect to the measurement means in a plane perpendicular to the direction of movement of the test piece. Furthermore the invention relates to a corresponding process.

2. Description of Related Art

A conventional measurement process for nondestructive and noncontact detection of faults in a test piece, especially a semi-finished metallic article, is induction measurement of eddy currents in the test piece. Here, the test piece is exposed to periodic alternating electromagnetic fields by means of a sinusoidally energized transmitting coil. The eddy currents induced thereby in the test piece, in turn, induce a periodic electrical signal in a coil arrangement used as a probe. The periodic electrical signal has a carrier oscillation according to the transmitter carrier frequency whose amplitude and/or phase is modulated by a fault in the test piece in a characteristic manner when the fault travels into the sensitive region of the probe. Conventionally, to scan the test piece, the latter is moved linearly with respect to the probe, but also arrangements with a rotating probe are known. One example of an eddy current measurement device with a linearly advanced test piece can be found in U.S. Pat. No. 5,175,498.

Another conventional measurement process for nondestructive and noncontact detection of faults in a test piece is known as magnetic stray flux measurement (or magnetic stray field measurement) in which, by means of an induction coil with a magnetic yoke, magnetization of the test piece is produced and the magnetic stray flux produced by the test piece is measured by means of a suitable sensor. Faults in the test piece are detected based on their effects on the magnetic stray flux. One example of such a stray flux measurement can be found in U.S. Pat. No. 4,445,088.

In order to be able to carry out an eddy current or stray flux measurement, the test piece must be supplied to the measurement device by means of a suitable guide means in a conventionally centered position which is exactly defined with respect to the measurement device, and this defined feed position is to be permanently maintained in operation. One example for this positioning means or guide means can be found in German Patent Application DE 198 22 986 A1 and corresponding U.S. Pat. No. 6,344,740 B1.

Since both in eddy current measurement and also in stray flux measurement the distance between the test piece and the measurement probe is relatively critical, it is important for the reliability and meaningfulness of the measurements to ensure the exact feed position of the test piece. Typically, the guide means for the test piece is not regularly monitored. Mainly, due to the rough environments in which eddy current and stray flux measurement devices are conventionally operated, for example, in steel mills, this can lead to the guide means for the test piece falling out of adjustment after a relatively short running time so that the reliability of the measurements can be a problem. In particular, the guide means is also exposed to the aging phenomena, for example, wear of the rolls. For a de-centered cylindrical test piece, this can lead to the same types of faults producing fault signals of different size depending on the position on the periphery of the test piece In stray flux measurement, where dragging probes are used, de-centering of the test piece leads to increased wear and increases the danger that the probe heads will rise briefly or entirely; this leads to more or less long insensitivity of the test system. A differing sensitivity depending on the position of the fault on the periphery also occurs in stray flux measurement since the magnet yokes are moving on a fixed orbit around the test piece, by which the magnetization power is modulated with the position on the periphery so that, with de-centering, identical faults are unequally detected depending on the radial angular position.

For eddy current measurement devices with probes revolving around the periphery of the test piece, measuring the distance between the probe head and test piece is known in order to be able to correct the measurement with respect to the distance which fluctuates in the course of a revolution, for example, as a result of de-centering or asymmetry of the cross section of the test piece. One example of this arrangement can be found in German Patent Application DE 40 03 330 A1.

German Patent Application DE 44 21 912 A1 discloses a device for centering the spindles of textile machines in which two laser triangulation sensors which are located around the spindle at an angle to one another are used to determine the position of the spindles.

German Patent Application DE 101 14 961 A1 discloses a process for determining the outside contour and orientation of rolled steel test pieces moving in the lengthwise direction, distributed in the peripheral direction of the test piece there being several sensors for shadow measurements. A similar process is described in German Patent Application DE 10 2006 048 954 A1, a shadow measurement being combined with a split-beam measurement.

SUMMARY OF THE INVENTION

A primary object of the invention to devise a device and a process for nondestructive and noncontact detection of faults in a test piece by means of eddy current or magnetic stray flux measurement with which the reliability of the measurement results will be increased.

This object is achieved in accordance with the invention by a device having a monitoring unit with at least three distance sensors arranged distributed around the test piece in the peripheral direction and facing the respective sensor for contactless detection of the distance between the surface of the test piece and the respective sensor, as well as a unit for evaluating the sensor signals, and with a corresponding process.

In the approach in accordance with the invention, it is advantageous that because there is a monitoring unit with at least three distance sensors arranged distributed around the test piece in the peripheral direction for contactless detection of the distance between the surface facing the respective sensor and the respective sensor as well as a unit for evaluating the sensor signals, the geometry or position of the test piece can be permanently determined and monitored, by which the reliability of eddy current measurement or stray flux measurement whose result depends largely on the distance between the probe and the surface of the test piece can be increased. Furthermore, the signals of the distance sensors can be used to control the eddy current and stray flux measurement means. Thus, the signal of the distance sensors can replace the obligatory input photoelectric barrier for ending signal suppression.

In the preparation for the test the monitoring unit can be used as a centering aid. Here, with a (straight) pattern test piece the measurement means can be aligned vertically and horizontally. The monitoring unit then continuously delivers the deviation from the center. For example, if there are wear phenomena on the inlet rolls, they can also be considered in the set-up.

In the actual test phase, the measurement means is supplied with test pieces which differ in cross-sectional geometry or whose cross-sectional geometry changes (for example, changing diameters for round material or deviations from a circle geometry for pipes, but also deviations in straightness of the lengthwise direction). In the test phase, the cross-sectional geometry of the test piece (i.e., dimensions and shape of the cross section) can be tested, but in the combination of geometry and center also the axial deviation of the straightness of the test piece. Therefore, deviations from the center can also occur for an ideally aligned test. They can be detected, and together with the cross-sectional geometry, can be qualitatively evaluated—for example, the current diameter and axial sagging of the test piece. The maximum axial sagging in mm/m is, for example, contractually agreed, because overly high deviations make a reliable test impossible, and increased wear can even destroy the measurement means. The manufacturer of pipes or rods will also guarantee a reliable degree of straightness to his customers.

Moreover, it is possible to validate the test process itself: only a given deviation of geometry and center is allowable for a valid test while, when a given limit is exceeded, these parts are logged as untested. For major deviations, the system could also be stopped to avoid greater damage to the measurement means. A recorded deterioration of straightness of the test material can, for example, also cause the user to subject his straightening machine to inspection.

Fundamentally, running alignment correction of the measurement means by way of a control circuit is also possible. However, due to the often large mass of the measurement means, in practice, this would often be associated with high cost. For smaller measurement means, for example, elastically suspended coils can be used which follow the test piece so that a servo design combined with the centering aid can be implemented here.

One embodiment of the invention is detailed by way of example below using the attached drawings.

DETAILED DESCRIPTION OF THE INVENTION

Figure 1:
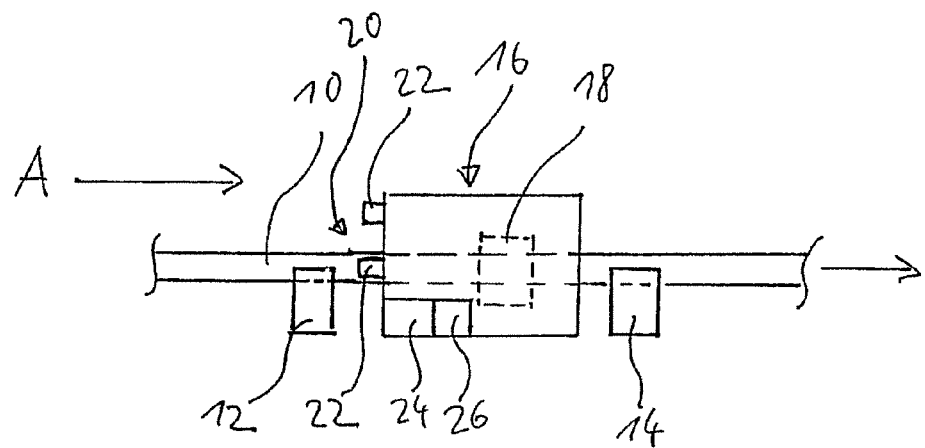
FIG. 1 is a schematic side view of one example of a device in accordance with the invention.

FIG. 1 is a schematic side view of one embodiment of a device in accordance with the invention for nondestructive and noncontact detection of faults in a test piece. The test piece 10 is typically a semi-finished industrial product and is advanced by an inlet-side positioning means 12 and an outlet-side guide means 14 with respect to a measurement means 16, and mainly, by means of the inlet side positioning means with respect to the measurement means 16, is positioned in a plane which is perpendicular to the direction of motion of the test piece 10.

Fundamentally, the measurement means 16 can be an eddy current measurement means or a means of measuring a magnetic stray flux. The measurement means 16 has a stationary measurement head 18 which is located on the test piece 10 or around the test piece 10.

Figure 2:
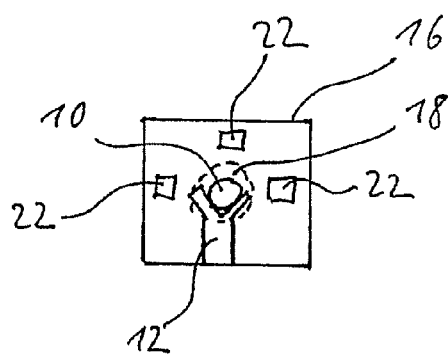
FIG. 2 shows a view of the device from FIG. 1 in the direction of arrow A.
Figure 3:
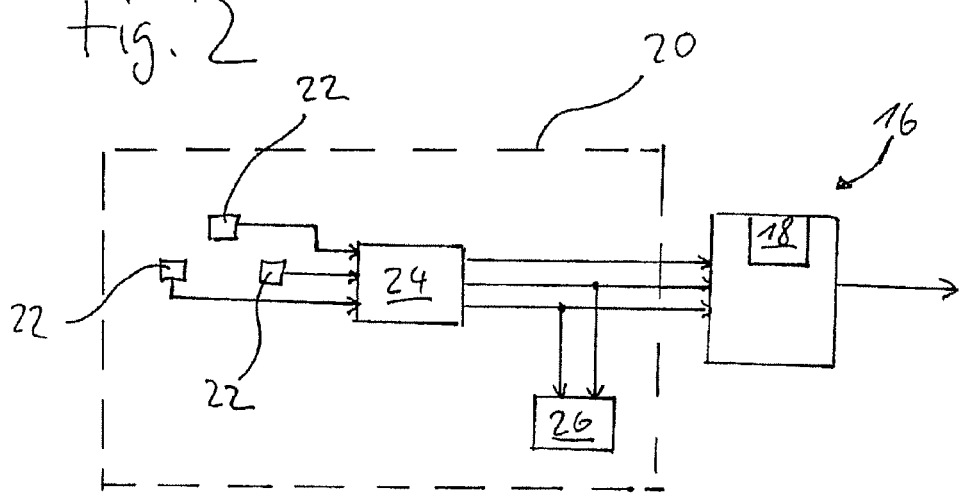
FIG. 3 is a block diagram of the device from FIG. 1.

FIGS. 1 & 2 show a test piece with a circular cross section. However, the device in accordance with the invention can also be used for test pieces with other cross sections, for example, rectangular cross sections.

At the inlet of the measurement means 16, there is a monitoring means 20 which has at least three contactless distance sensors 22 which are arranged distributed around the test piece 10 in order to detect the distance between the surface of the test piece 10 facing the respective sensor 22, and the respective sensor 22. The sensors 22 are preferably optical distance sensors as are used for laser triangulation. However, other types of sensors can also be used, for example, laser scanners with time measurement of shadowing, measurement of shadowing by means of a video camera, capacitive sensors, inductive sensors or ultrasonic sensors. Suitable laser triangulation sensors are offered, for example, by the company Baurner of Frauenfeld, Switzerland.

Preferably, the sensors 22 are arranged distributed in the peripheral direction of the test piece 10 such that one sensor is at the top and the other two sensors are laterally at an angle of roughly 90° relative to the top sensor. Mathematically, an offset of the sensors by 120°, i.e., a uniformly distributed arrangement, would be preferred. In any case, in this uniform arrangement, scale and other dirt can easily accumulate on the optical distance sensors located at the bottom of the test piece, and thus, attenuate the laser beam. Depending on the required accuracy of the measurement, more than three sensors 22 can also be used.

Furthermore, the sensors 22 are preferably located in a common plane, specifically a plane perpendicularly to the direction of advance of the test piece 10.

While a design with stationary sensors 22 can be most easily implemented and is generally adequate, especially for test pieces 10 with a circular cross section, it is also possible to make the sensors 22 able to rotate or swing around the test piece 10 individually, or as a whole, (in the latter case, a slip ring or transformer can be omitted). These designs are feasible mainly for test pieces with a rotationally unsymmetrical cross section, for example, a square or rectangular cross section, and also for pipes which are rarely perfectly round.

The signals of the sensors 22 are supplied to an evaluation unit 24 which performs the following functions: the position of the test piece 10 relative to the measurement means 16 is determined in a plane which is perpendicular to the direction of motion of the test piece 10, i.e., the centering of the test piece 10 with respect to the measurement means 16 is determined. In preparation for the test, the monitoring means 20 can thus be used as a centering aid; using a (straight) pattern test piece, the measurement means 16 and the measurement head 18 are aligned horizontally and vertically relative to the test piece, i.e., relative to the positioning means 12, using the determined deviation from the center (here, conventionally the measurement means 16 or the measurement head 18 is moved relative to the test piece 10, i.e., relative to the positioning means 12). In the actual test phase, deviations from the center can be detected by the monitoring means 20.

Furthermore, the geometry of the test piece is determined from the sensor signals (for example, if the test piece 10 is cylindrical, the diameter of the test piece 10 is determined). In the combination of the geometry and centricity, the straightness of the test piece 10 can be determined. Moreover, it is determined from the sensor signals whether there is a test piece at all in order to control the measurement means 16 accordingly (here, especially the function of a conventional input photoelectric barrier for ending signal suppression can be implemented).

Preferably, there is an optical display means 26 in order to display the determined diameter of the test piece 10 and/or the determined test piece position. The display means 26 can be made as a LED display for de-centering, for example, in the form of a target disk, and for the diameter.

The determined position of the test piece 10 is incorporated in the evaluation of the eddy current measurement or the stray flux measurement and can be supplied to the measurement means 16 for this purpose. Furthermore, the determined position of the test piece 10 can be recorded for logging purposes also as a function of time. Alternatively or additionally, the determined position of the test piece 10 can be used by the positioning means 12 to correct the position of the test piece 10 to a setpoint.

The determined diameter and the determined straightness of the test piece 10 can also be used in the evaluation of the eddy current measurement and the stray flux measurement and can be supplied to the measurement means 16 for this purpose. Furthermore, the determined diameter and the determined straightness of the test piece 10 can be recorded as a function of time in order to enable display and logging of the properties of the test piece. In particular, a statistical evaluation can also be performed here.

Furthermore, the evaluation unit 24 has a "photoelectric barrier output" for controlling the measurement means 16 depending on whether there is a test piece 10 or not.

The monitoring unit 20 with the sensors 22, the evaluation unit 24 and the display means 26 can be made as a separate unit or it can be integrated into the measurement means 16. In any case, the position of the sensors 22 with respect to the measurement means 16 and the measurement head 18 must be fixed in order to be able to determine the centering of the test piece 10 with respect to the measurement head 18.

What is claimed is:

1. Device for nondestructive and noncontact detection of faults in a test piece, comprising:
    a stationary measurement means for taking an eddy current or magnetic stray flux measurements on a test piece and for producing measurement signals representative of said measurements; and
    means for positioning the test piece with respect to the measurement means in a plane perpendicular to the direction of movement of the test piece and for continuously advancing the test piece along a linear path of movement relative to the measurement means,
    a monitoring unit with at least three distance sensors arranged distributed in a peripheral direction around the path of movement of the test piece for contactless detection of the distance between the surface of the test piece and each of the sensors and for producing position signals representative of the distances between the test piece and each of the sensors, and
    a unit for evaluating said position signals to determine the position of the test piece with respect to said measurement means and
    wherein said measurement means is adapted for using the determined position of the test piece in evaluation of the eddy current measurement or stray flux measurement.

2. Device in accordance with claim 1, wherein the evaluation unit is adapted for determining, from said signals, the position of the test piece relative to the measurement means in a plane which is perpendicular to the direction of motion of the test piece.

3. Device in accordance with claim 1, wherein the evaluation unit is adapted to determine at least one of the cross-sectional shape and straightness of the test piece from said signals.

4. Device in accordance with claim 1, wherein the evaluation unit is adapted to determine from said signals whether or not there is a test piece in position for measurement by the measurement means.

5. Device in accordance with claim 1, wherein the distance sensors are located in a single plane.

6. Device in accordance with claim 1, wherein the distance sensors are one of optical, capacitive, inductive and ultrasonic sensors.

7. Device in accordance with claim 1, wherein the distance sensors are laser triangulation sensors.

8. Device in accordance with claim 1, further comprising an optical display means for displaying at least one of the diameter and position of the test piece determined by the evaluation means.

9. Device in accordance with claim 1, wherein the distance sensors are mounted to rotate or swing around the test piece individually or as a unit.

10. Process for nondestructive and noncontact detection of faults in a test piece, comprising the steps of:
    continuously advancing a test piece, relative to a measurement means eddy current or magnetic stray flux measurement means, in a plane which is perpendicular to the direction of advance of the test piece;
    using the using eddy current or magnetic stray flux measurement means for detecting the existence of flaws in the test piece which is continuously advanced relative to the measurement means and
    using at least three noncontact distance sensors which are arranged distributed in a peripheral direction around the test piece for detecting the distance between the surface of the test piece facing each of the sensors and the respective sensor and producing position signals representative of the distances between each of the sensors and the test piece, and
    evaluating said position signals to determine the position of the test piece with respect to said measurement means and using the determined position of the test piece in evaluation of the eddy current measurement or stray flux measurement.

11. Process in accordance with claim 10, determining the position of the test piece is relative to the measurement means in a plane which is perpendicular to the direction of advance of the test piece from the evaluation of said signals.

12. Process in accordance with claim 11, wherein the determined position of the test piece is used to correct the position of the measurement means relative to the test piece to a setpoint.

13. Process in accordance with claim 10, wherein at least one of the cross-sectional shape and straightness of the test piece is determined from said signals.

14. Process in accordance with claim 13, wherein at least one of the cross-sectional shape and straightness of the test piece is recorded as a function of time.

15. Process in accordance with claim 10, wherein whether or a test piece is present in position for measurement by the measurement means is determined from said signals, and the measurement means is controlled accordingly.

* * * * *